United States Patent
Govari

(10) Patent No.: US 10,726,588 B2
(45) Date of Patent: Jul. 28, 2020

(54) MAGNETIC RESONANCE IMAGING (MRI) IMAGE FILTRATION ACCORDING TO DIFFERENT CARDIAC RHYTHMS

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 105 days.

(21) Appl. No.: 16/175,958

(22) Filed: Oct. 31, 2018

(65) Prior Publication Data

US 2020/0134889 A1   Apr. 30, 2020

(51) Int. Cl.
| | | |
|---|---|---|
| A61B 5/02 | (2006.01) | |
| G06K 9/00 | (2006.01) | |
| G06T 11/00 | (2006.01) | |
| A61B 5/055 | (2006.01) | |
| G01R 33/567 | (2006.01) | |

(52) U.S. Cl.
CPC ............ G06T 11/008 (2013.01); A61B 5/055 (2013.01); G01R 33/5676 (2013.01); A61B 2576/023 (2013.01); G06T 2207/30048 (2013.01)

(58) Field of Classification Search
USPC ....... 382/100, 103, 107, 128–134, 162, 168, 382/173, 199, 220, 254, 274, 276, 382/285–291, 305, 312; 378/4, 21; 600/508, 522
See application file for complete search history.

(56) References Cited

U.S. PATENT DOCUMENTS

| | | | |
|---|---|---|---|
| 7,756,576 B2 | 7/2010 | Levin | |
| 7,848,787 B2 | 12/2010 | Osadchy | |
| 7,848,789 B2 | 12/2010 | Govari et al. | |
| 7,869,865 B2 | 1/2011 | Govari et al. | |
| 8,320,711 B2* | 11/2012 | Altmann | A61B 5/061 382/128 |
| 8,456,182 B2 | 6/2013 | Bar-Tal et al. | |
| 2002/0026115 A1 | 2/2002 | Nehrke et al. | |
| 2004/0264752 A1 | 12/2004 | Cline et al. | |
| 2009/0148012 A1* | 6/2009 | Altmann | A61B 5/06 382/128 |
| 2009/0275822 A1 | 11/2009 | Detsky et al. | |

(Continued)

OTHER PUBLICATIONS

Stuber, Matthias, "Submillimeter Three-dimensional Coronary MR Angiography with Real-time Navigator Correction: Comparison of Navigator Locations", Radiology,vol. 212, No. 2,Aug. 1, 1999 (Aug. 1, 1999), pp. 579-587, XP055648515,USISSN: 0033-8419.

(Continued)

Primary Examiner — Seyed H Azarian
(74) Attorney, Agent, or Firm — Notaro, Michalos & Zaccaria P.C.

(57) ABSTRACT

A method includes receiving a plurality of voxel values corresponding to respective locations in a heart, which are acquired using magnetic resonance imaging (MRI). Voxel values that, in spite of (i) corresponding to a same location in the heart and (ii) being gated to a same phase of an electrocardiogram (ECG) cycle of the heart, differ by more than a predefined difference, are identified. An image of at least a portion of the heart is reconstructed from the plurality of voxel values excluding at least the identified voxel values.

8 Claims, 3 Drawing Sheets

(56) References Cited

U.S. PATENT DOCUMENTS

| | | | |
|---|---|---|---|
| 2013/0338520 A1* | 12/2013 | Govari | A61B 18/1492 |
| | | | 600/522 |
| 2014/0303480 A1 | 10/2014 | Lai | |
| 2015/0018698 A1* | 1/2015 | Safran | G06F 17/11 |
| | | | 600/508 |
| 2015/0192653 A1 | 7/2015 | Sharif et al. | |
| 2016/0140751 A1* | 5/2016 | Jafarkhani | A61B 5/0044 |
| | | | 382/131 |
| 2017/0097401 A1 | 4/2017 | Bannae | |
| 2018/0228554 A1* | 8/2018 | Strommer | A61B 6/541 |

OTHER PUBLICATIONS

Manjon, J V, et a;., "Non-local MRI Upsampling", Medical Image Analysis, Oxford University Press, Oxofrd, 6B, vol. 14, No. 6,Dec. 1, 2010 (Dec. 1, 2010), pp. 784-792, XP027141540,ISSN: 1361-8415.

Extended European search report for corresponding European patent application No. EP 19206241.2, dated Jan. 2, 2020.

Odille et al., Model-based reconstruction for cardiac cine MRI without ECG or breath holding, Magnet Resonance in Medicine, vol. 63, 1247-1257, Issue 5, Apr. 23, 2010.

* cited by examiner

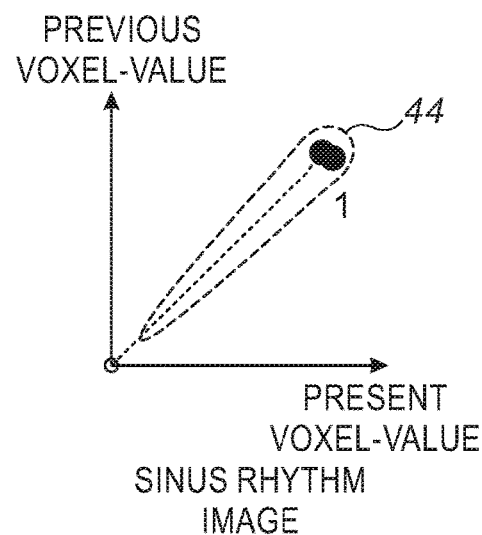
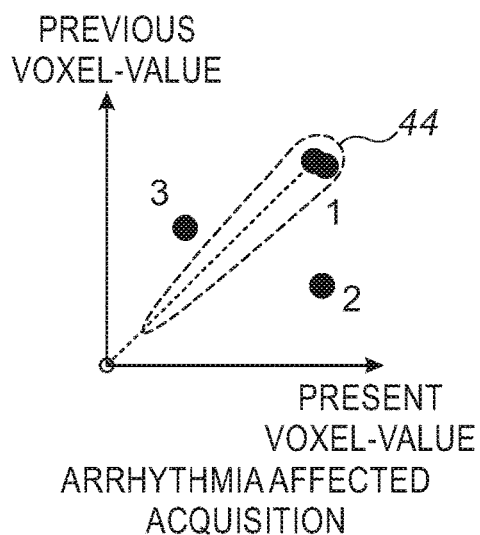
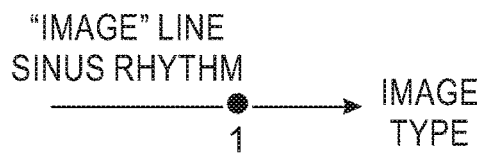
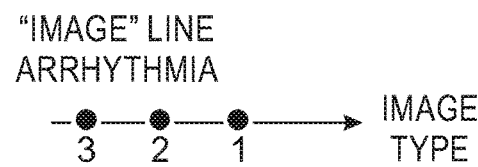
*FIG. 2A*      *FIG. 2B*
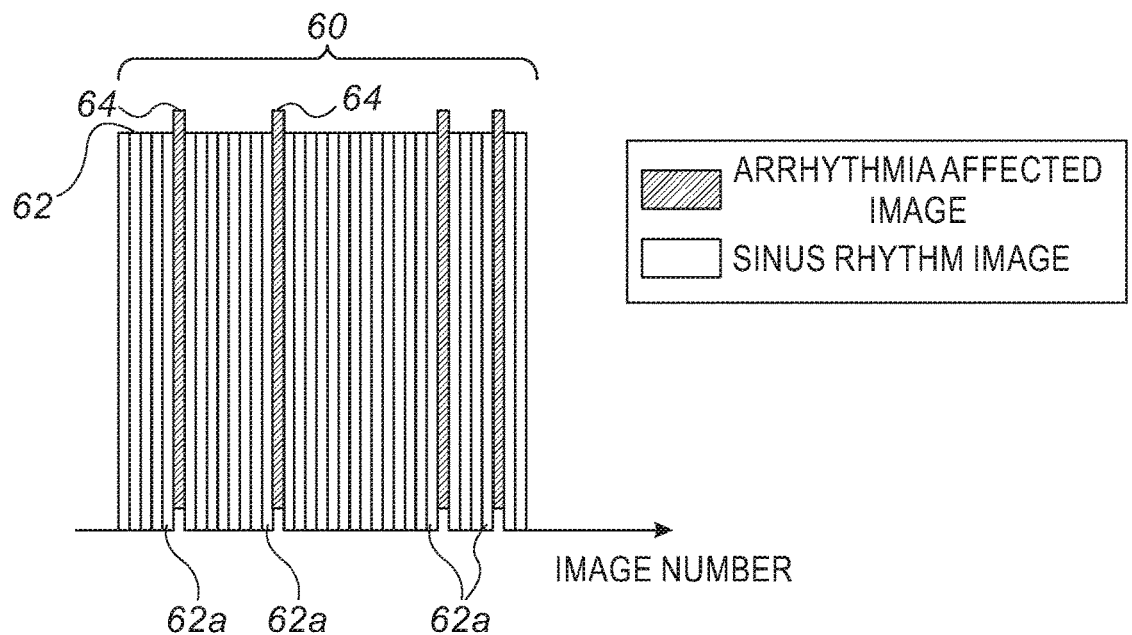
*FIG. 3*

MAGNETIC RESONANCE IMAGING (MRI) IMAGE FILTRATION ACCORDING TO DIFFERENT CARDIAC RHYTHMS

FIELD OF THE INVENTION

The present invention relates generally to medical magnetic resonance imaging (MRI), and particularly to cardiac MRI.

BACKGROUND OF THE INVENTION

Various techniques have been proposed for reducing the degrading impact of image artifacts on cardiac MRI studies. For example, U.S. Patent Application Publication 2009/0275822 describes a series of MR image frames that depict a subject's heart at successive cardiac phases. Delayed enhancement of infarcted myocardium is depicted in some of the image frames by administering a contrast agent prior to data acquisition. Data acquisition is performed in a single breath hold. The acquired MR image frames depict contrast between blood, viable myocardium and nonviable myocardium, and they depict left ventricle wall thickness and wall thickening throughout the cardiac cycle. In an embodiment, a scatter plot, which has the T1* versus steady state value of every image frame pixel is fed into a fuzzy clustering process and the pixels are automatically separated into three clusters. The pixels can then be color coded on a displayed image frame according to the tissue type which it has been classified-infarcted myocardium, normal myocardium or blood. From the probability values produced by the fuzzy clustering process it is also possible to segment pixels made up of a mixture of infarcted myocardium and normal myocardium. The number of pixels in this resulting "gray zone" indicated by this mixture of two tissue types has been shown to predict which subjects are more likely to suffer cardiac arrhythmias.

As another example, U.S. Patent Application Publication 2015/0192653 describes systems and methods for cardiac MRI that allow for continuous un-interrupted acquisition without any ECG/cardiac gating or synchronization that achieves the required image contrast for imaging perfusion defects. The invention also teaches an accelerated image reconstruction technique that is tailored to the data acquisition scheme and minimizes or eliminates dark-rim image artifacts. The invention further enables concurrent imaging of perfusion and myocardial wall motion (cardiac function), which can eliminate the need for separate assessment of cardiac function (hence shortening exam time), and/or provide complementary diagnostic information in CAD patients. In some embodiments, radial-geometry-based acquisition method and sampling method are applied to generate eight (8) real-time frames per second. No external ECG signal or other forms of cardiac synchronization is needed for this method.

SUMMARY OF THE INVENTION

An embodiment of the present invention provides a method including receiving a plurality of voxel values corresponding to respective locations in a heart, which are acquired using magnetic resonance imaging (MRI). Voxel values that, in spite of (i) corresponding to a same location in the heart and (ii) being gated to a same phase of an electrocardiogram (ECG) cycle of the heart, differ by more than a predefined difference, are identified. An image of at least a portion of the heart is reconstructed from the plurality of voxel values excluding at least the identified voxel values.

In some embodiments, identifying the voxel values that differ by more than the predefined difference includes constructing a scatter plot including multiple data points in a plane whose first and second axes denote voxel values acquired in respective first and second MRI acquisitions, wherein each data point represents the voxel values at a given location in the heart in the first and second MRI acquisitions, and identifying one or more data points that fall outside a predefined region in the plane.

In some embodiments, reconstructing the image includes skipping reconstruction of any image that includes an acquisition taken during an identified arrhythmia.

In an embodiment, the method further includes, in response to excluding the voxel values, adjusting a thickness of the reconstructed image.

In another embodiment, the method further includes, in response to excluding the voxel values, adjusting a reconstruction filter used for reconstructing the image.

There is additionally provided, in accordance with an embodiment of the present invention, a system including a memory and a processor. The memory is configured to store a plurality of voxel values corresponding to respective locations in a heart, which are acquired using magnetic resonance imaging (MRI). The processor is configured to identify voxel values that, in spite of (i) corresponding to a same location in the heart and (ii) being gated to a same phase of an electrocardiogram (ECG) cycle of the heart, differ by more than a predefined difference. The processor is further configured to reconstruct an image of at least a portion of the heart from the plurality of voxel values excluding at least the identified voxel values.

The present invention will be more fully understood from the following detailed description of the embodiments thereof, taken together with the drawings in which:

BRIEF DESCRIPTION OF THE DRAWINGS

FIGS. 2A and 2B are schematic, illustrative scatterplots comprising voxel-value patterns and respective image types according to different cardiac rhythms, in accordance with an embodiment of the present invention;

FIG. 3 is a schematic, pictorial diagram that illustrates image filtration according to different cardiac rhythms, in accordance with an embodiment of the present invention.

DETAILED DESCRIPTION OF EMBODIMENTS

Overview

Figure 1:
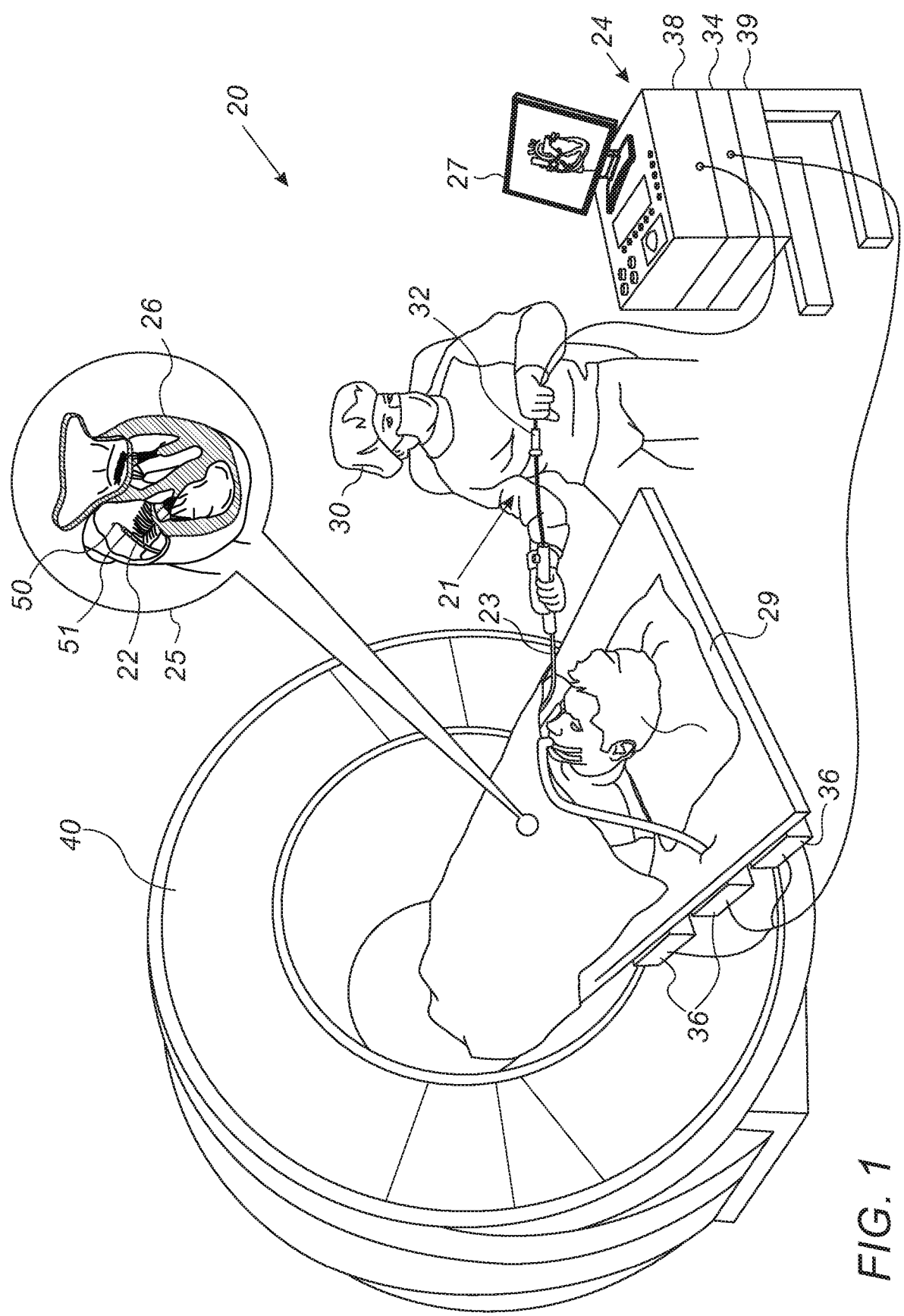
FIG. 1 is a schematic, pictorial illustration of a catheter-based electroanatomical mapping system, in accordance with an embodiment of the present invention.

Cardiac magnetic resonance imaging (MRI) is challenging due to the motion of the heart, which may introduce motion-artifacts into the MRI images. One method to minimize motion-artifacts is to gate the MRI acquisitions using an electrocardiogram (ECG) signal of the heart. An ECG signal is indicative, for example, of the systolic and diastolic phases of the heart over a heartbeat period. Therefore, using ECG gating, a series of MRI acquisitions of the heart can be taken at specific, recurring time-intervals, when, for example, the heart is at its maximal dilation and nearly static for a brief duration. An MRI image reconstructed from such ECG gated acquisitions, which have all been acquired at a particular phase of the cardiac cycle, would be relatively free of motion-artifacts despite the acquisitions being collected over the duration of several heartbeats.

However, for the ECG gating to be meaningful (i.e., indicative of the phase of the heart), the heart has to beat in a regular sinus rhythm. Thus, the occurrence of an irregular beat, such as an ectopic beat, may significantly distort an MRI image (even if gating is used) by, for example, the reconstructed image mixing phases of the dilated heart and the contracted heart.

Embodiments of the present invention that are described hereinafter filter out, from a series of MRI signal acquisitions (i.e., before the images were actually reconstructed), signal acquisitions that would be distorted due to an arrhythmic activity, such as an ectopic beat. The filtration is typically done at the MRI signal level, before the acquired signals are computer-processed into an image (i.e., a slice).

In some embodiments, a processor receives a plurality of voxel values corresponding to respective locations in a heart, which are acquired using MRI. The processor identifies voxel values that, in spite of (i) corresponding to a same location in the heart and (ii) being gated to the same phase of an electrocardiogram (ECG) cycle of the heart, differ by more than a predefined difference. For example, the processor may compare voxel-values of selected voxels between two successive acquisitions. Based on the identification, the processor reconstructs an image of at least a portion of the heart from the plurality of voxel values excluding at least the identified voxel values.

In an embodiment, the processor analyzes the voxel-values by examining a voxel-value pattern, wherein the voxel-value pattern is indicative of a type of a cardiac rhythm. For successive acquisitions that are taken during a normal sinus rhythm, there is no substantial change of voxel values for any given selected voxel. If there is an irregular beat, the voxel value for some voxels in the heart changes, compared with previous gated voxel values. Based on the indication that the voxel-value pattern provides, the processor determines whether a later acquisition of each of the two successive acquisitions was taken during an arrhythmia (i.e., by comparing "present" voxel values, with "previous" voxel values). In an embodiment, the processor skips the reconstruction of any image that requires an acquisition taken during an identified arrhythmia.

If the acquisitions are made with enough overlap, to have sufficient redundancy in voxel values, then excluding the identified voxel values may not be visually noticeable in the series of images, or noticeable in a derived visualization such as a volume rendering. Otherwise, in order not to introduce noticeable discontinuities due to the disclosed image filtration, the slice thickness of the reconstructed images could be adjusted and/or a smoother reconstruction filter chosen.

Typically, the processor is programmed in software containing a particular algorithm that enables the processor to conduct each of the processor-related steps and functions outlined above.

The resulting filtered series of MRI images enables a physician to derive various visual representations of at least a portion of the heart, which are relatively free of motion-artifacts, despite being acquired during the presence of an arrhythmia. The disclosed MRI image filtration according to different cardiac rhythms may therefore facilitate the successful imaging of a patient's heart with an arrhythmia, and may therefore assist in the diagnosis and therapy of such patients.

System Description

FIG. 1 is a schematic, pictorial illustration of a catheter-based electroanatomical mapping system 20, in accordance with an embodiment of the present invention. System 20 comprises a catheter 21, having a distal end 22 that is navigated by a physician 30 into a heart 26 of a patient 28 via the vascular system. In the pictured example, physician 30 inserts distal end 22 through a sheath 23, while manipulating distal end 22 using a manipulator 32 near the proximal end of the catheter. As shown in inset 25, distal end 22 comprises a magnetic position sensor 51 and an ablation electrode 50.

The proximal end of catheter 21 is connected to a control console 24. Console 24 comprises a processor 39, typically a general-purpose computer, with suitable front end and interface circuits 38 for receiving signals from catheter 21, as well as for applying energy via catheter 21 to ablate tissue in heart 26 and for controlling the other components of system 20. Console 24 also comprises a driver circuit 34, configured to drive magnetic field generators 36.

During navigation of distal end 22 in heart 26, console 24 receives position and direction signals from sensor 51 in response to magnetic fields from external field generators 36. Magnetic field generators 36 are placed at known positions external to patient 28, e.g., below a table 29 upon which the patient is lying. These position signals are indicative, for example, of the position of an ablation electrode 50 in the coordinate system of the position tracking system.

The method of position and direction sensing using external magnetic fields is implemented in various medical applications, for example, in the CARTO™ systems, produced by Biosense-Webster, Irvine, Calif.

In alternative embodiments, the location of distal end 22 is tracked during the procedure using an Advanced Current Location (ACL) technique. In the ACL technique, a plurality of external electrodes is coupled to the body of patient 28. Electric currents are passed between an electrode of the catheter, such as electrode 50, and the external electrodes. Based on respectively measured impedances, processor 39 calculates the location of electrode 50 within the patient's heart.

The ACL technique of tracking electrode locations is implemented in various medical applications, for example, in the CARTO™ system, produced by Biosense-Webster Inc. (Irvine, Calif.) and is described in detail in U.S. Pat. Nos. 8,456,182, 7,756,576, 7,869,865, 7,848,787, and 7,848,789, whose disclosures are all incorporated herein by reference.

As seen, patient 28 is placed inside an MRI system 40. Console 24 is configured to acquire, reconstruct, and present to physician 30 images of at least a portion of heart 26, for example, on display 27. MRI system 40 may be used, for example, to show a portion of heart 26 in real-time, or, as another example, for acquiring and reconstructing images of a portion of heart 26, for creating an anatomical map of the portion of heart 26. In some embodiments, the MRI images are acquired on a different system (i.e., MRI system 40 is absent), and are uploaded to processor 39 for the disclosed image filtration process.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 39 runs a dedicated algorithm as disclosed herein, including in FIG. 4, that enables processor 39 to perform the disclosed steps, as further described below.

MRI Image Filtration According to Different Cardiac Rhythms

As noted above, voxel values that in spite of (i) corresponding to a same location in the heart and (ii) being gated to a same phase of an electrocardiogram (ECG) cycle of the heart, differ by more than a predefined difference, can be characterized and further analyzed using scatterplots.

FIGS. 2A and 2B are schematic, illustrative scatterplots comprising voxel-value patterns and respective image types according to different cardiac rhythms, in accordance with an embodiment of the present invention.

FIG. 2A is a schematic voxel-value pattern plot for three successive, ECG-gated, MRI acquisitions taken during a normal sinus rhythm. The three successive acquisitions correspond to the same voxel, i.e., the same location in the heart. From among the three acquisitions, each successive pair of acquisitions yields data point in the voxel-value pattern plot. As such, two data points are shown in the figure. A boundary 44 about the bisector line marks an area where any two successive acquisitions with a voxel-pattern value falling inside can be used. Thus, boundary 44 predefines the tolerable difference between voxel values that, if exceeded, warrants discarding of the acquisitions.

As seen, the voxel-value pattern shows two values "1" that both fall inside the bounded area, which means that the related acquisitions were taken during a normal sinus rhythm. Note that the allowed variation in voxel-pattern values inside the bounded area is due to normal heart rate variations. Accordingly, the "image" type shown on a respective image line is also characterized as "1," meaning that the image was reconstructed from acquisitions taken during a normal sinus rhythm.

FIG. 2B is a schematic voxel-value plot for five successive ECG-gated MRI acquisitions where the two latter acquisition were taken during an arrhythmia. As seen, the arrhythmia is characterized by the two latter voxel-values changing outside the area bounded by boundary 44. Accordingly, additional "image" types on an image line are marked as types "2" and "3," being characterized as reconstructions using an acquisition taken during an arrhythmia (and thus images "2" and "3" are of a degraded quality).

The example illustrations shown in FIGS. 2A and 2B are chosen purely for the sake of conceptual clarity. In an embodiment, when processor 39 identifies a deviation of the voxel-pattern from the bisector line beyond a given percentage (i.e., relative change in the MRI signal) as determined by a precalculated boundary 44, the processor characterizes an image using the later acquisition as an arrhythmia-affected image. Alternatively or additionally, other criteria may be set, such as a change that exceeds a predefined difference in the MRI signal.

FIG. 3 is a schematic, pictorial diagram that illustrates a method for image filtration according to different cardiac rhythms, in accordance with an embodiment of the present invention. According to legend 65, a given series 60 of MRI images comprises two types of images: images 62 that are reconstructed using acquisitions taken during sinus rhythm, and images 64 whose reconstruction requires an acquisition taken during an arrhythmia. Each image 62a is an acceptable image that the later, i.e., successive image 64, is filtered out of series 60 by processor 39 before it is reconstructed.

In an embodiment, in the exemplified case, series 60 comprises thin-slice (e.g., sub millimeter) images, so as to ensure that skipping an image 64 will not hamper the diagnostic quality of series 60.

Figure 4:
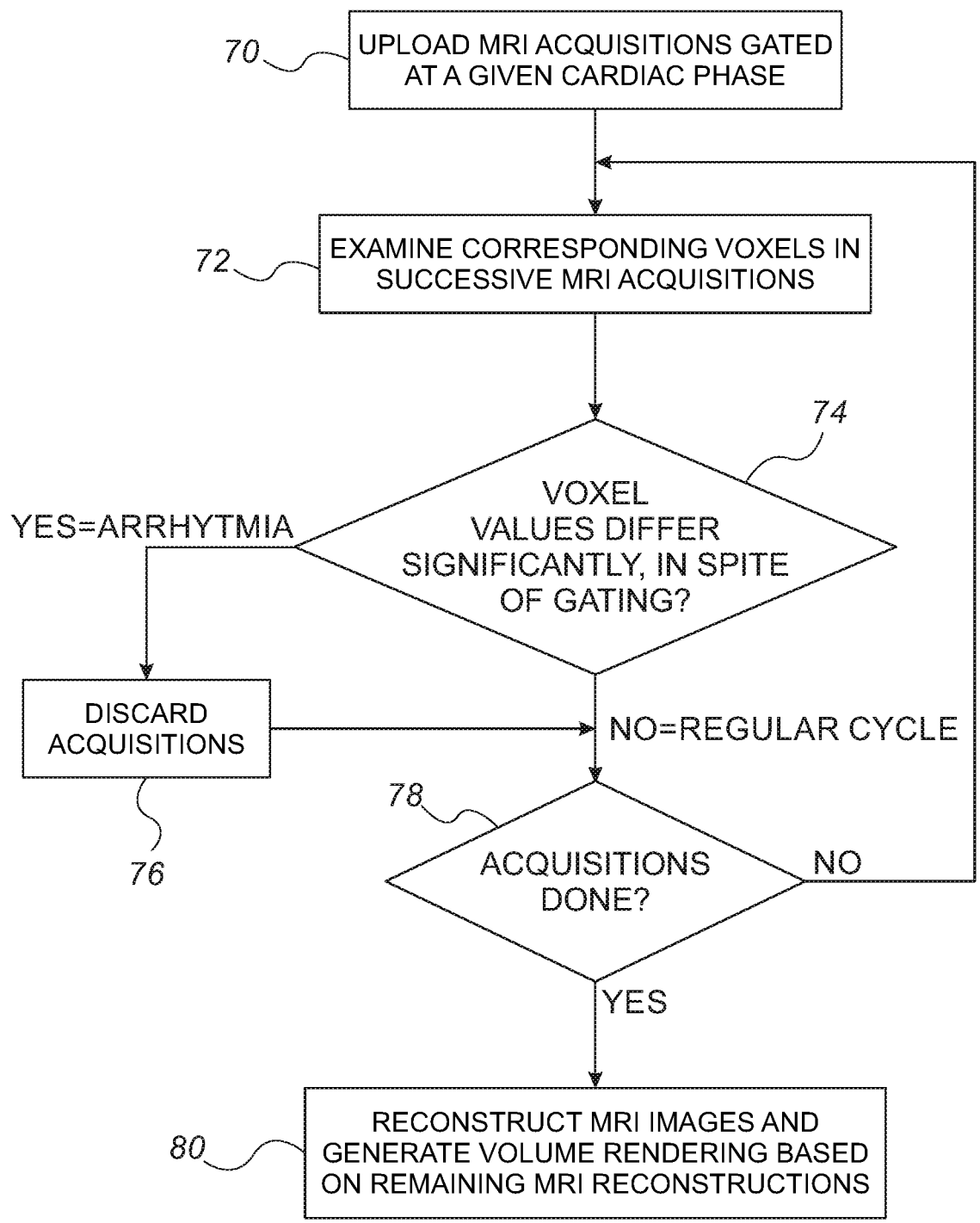
FIG. 4 is a flow chart that schematically illustrates a method and algorithm for image filtration according to different cardiac rhythms, in accordance with an embodiment of the present invention.

FIG. 4 is a flow chart that schematically illustrates a method and algorithm for image filtration according to different cardiac rhythms, in accordance with an embodiment of the present invention. The algorithm according to the present invention drives a process that begins at an MRI acquisitions uploading step 70, in which physician 30 uploads, from memory 33, MRI acquisitions ECG-gated at a given cardiac phase. Typically, a reconstruction using the acquisitions will generate at least one MRI image. Next, processor 28 examines corresponding voxels in successive MRI acquisitions, at a voxel-value comparison step 72. In an analysis step 74, using the dedicated algorithm, processor 28 isolates from the examined acquisitions (e.g., by tagging bad acquisitions) such that their voxel values differ significantly (in spite of using gating) from their respective predecessor acquisition's values. Then, processor 28 discards the isolated acquisitions, at a filtering out step 76.

At a next step, processor 28 checks if remaining acquisitions are sufficient for reconstructing the image series (i.e., all remaining needed acquisitions were done), at a reconstruction decision step 78. If there in not enough acquisitions, the process returns to step 72 to search for additional data. Otherwise, at a reconstruction step 80, processor 28 reconstructs the MRI images and generates volume rendering based on the remaining reconstructions. For example, the processor skipped reconstructing any image of the MRI series of images (e.g., an image 64 of series 60) that requires using an acquisition classified as taken during an arrhythmia. Finally, using the filtered series of MRI images, processor 28 generates a representation of the imaged heart, such as a volume rendering, at a representation step 78.

The example algorithm shown in FIG. 4 is chosen purely for the sake of conceptual clarity. The present invention also comprises additional steps of the algorithm, such as presenting an estimated type of arrhythmic pattern that caused an image to be filtered out of the series, which have been omitted from the disclosure herein purposely in order to provide a more simplified flow chart.

Although the embodiments described herein mainly address cardiac MRI imaging, the methods and systems described herein can also be used in other applications, such as in cardiac imaging using computed tomography (CT) or C-arm.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving a plurality of voxel values corresponding to respective locations in a heart, which are acquired using magnetic resonance imaging (MRI);

identifying voxel values that, in spite of (i) corresponding to a same location in the heart and (ii) being gated to a same phase of an electrocardiogram (ECG) cycle of the heart, differ by more than a predefined difference; and reconstructing an image of at least a portion of the heart from the plurality of voxel values excluding at least the identified voxel values, wherein identifying the voxel values that differ by more than the predefined difference comprises:

constructing a scatter plot comprising multiple data points in a plane whose first and second axes denote voxel values acquired in respective first and second MRI acquisitions, wherein each data point represents the voxel values at a given location in the heart in the first and second MRI acquisitions; and identifying one or more data points that fall outside a predefined region in the plane.

2. The method according to claim 1, wherein reconstructing the image comprises skipping reconstruction of any image that comprises an acquisition taken during an identified arrhythmia.

3. The method according to claim 1, and comprising, in response to excluding the voxel values, adjusting a thickness of the reconstructed image.

4. The method according to claim 1, and comprising, in response to excluding the voxel values, adjusting a reconstruction filter used for reconstructing the image.

5. A system, comprising:

a memory, which is configured to store a plurality of voxel values corresponding to respective locations in a heart, which are acquired using magnetic resonance imaging (MRI); and a processor, which is configured to:

identify voxel values that, in spite of (i) corresponding to a same location in the heart and (ii) being gated to a same phase of an electrocardiogram (ECG) cycle of the heart, differ by more than a predefined difference; and reconstruct an image of at least a portion of the heart from the plurality of voxel values excluding at least the identified voxel values, wherein the processor is configured to identify the voxel values that differ by more than the predefined difference by:

constructing a scatter plot comprising multiple data points in a plane whose first and second axes denote voxel values acquired in respective first and second MRI acquisitions, wherein each data point represents the voxel values at a given location in the heart in the first and second MRI acquisitions; and identifying one or more data points that fall outside a predefined region in the plane.

6. The system according to claim 5, wherein the processor is configured to reconstruct the image by skipping reconstruction of any image that comprises an acquisition taken during an identified arrhythmia.

7. The system according to claim 5, wherein the processor is further configured to, in response to excluding the voxel values, adjust a thickness of the reconstructed image.

8. The system according to claim 5, wherein the processor is further configured to, in response to excluding the voxel values, adjust a reconstruction filter used for reconstructing the image.

* * * * *